US010653621B2

(12) United States Patent
Wu et al.

(10) Patent No.: US 10,653,621 B2
(45) Date of Patent: May 19, 2020

(54) BIODEGRADABLE DRUG DELIVERY SYSTEMS FOR THE SUSTAINED RELEASE OF PROTEINS (71) Applicant: Allergan, Inc., Irvine, CA (US)

(72) Inventors: Cindy W. Wu, Foothill Ranch, CA (US); Michael R. Robinson, Irvine, CA (US); James A. Burke, Santa Ana, CA (US); Patrick M. Hughes, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 1603 days.

(21) Appl. No.: 14/037,528

(22) Filed: Sep. 26, 2013

(65) Prior Publication Data

US 2014/0086974 A1 Mar. 27, 2014

Related U.S. Application Data (60) Provisional application No. 61/706,516, filed on Sep. 27, 2012.

(51) Int. Cl.
*A61K 9/00* (2006.01)
*A61K 39/395* (2006.01)
*A61F 9/00* (2006.01)
*A61K 47/34* (2017.01)

(52) U.S. Cl.
CPC .......... *A61K 9/0051* (2013.01); *A61F 9/0017* (2013.01); *A61K 39/3955* (2013.01); *A61K 47/34* (2013.01)

(58) Field of Classification Search
CPC .................................................. A61K 9/0051
See application file for complete search history.

(56) References Cited

U.S. PATENT DOCUMENTS

| 4,853,224 A | 8/1989 | Wong |
| 4,997,652 A | 3/1991 | Wong |
| 5,443,505 A | 8/1995 | Wong et al. |
| 6,309,669 B1 | 10/2001 | Setterstrom et al. |
| 7,759,472 B2 | 7/2010 | Shima et al. |
| 7,931,909 B2 | 4/2011 | Hughes et al. |

(Continued)

FOREIGN PATENT DOCUMENTS

| WO | WO 2003/025019 | 3/2003 |
| WO | WO 2005/110436 | 11/2005 |

(Continued)

OTHER PUBLICATIONS

Bendas et al. (1999) "Targetability of novel immunoliposomes prepared by a new antibody conjugation technique" *Int J Pharm.* Apr. 20, 1999;181(1):79-93.

(Continued)

*Primary Examiner* — Paul W Dickinson
(74) *Attorney, Agent, or Firm* — Rosemarie Pilpa (57) ABSTRACT

Biodegradable drug delivery systems, such as extruded implants, for the sustained delivery of a protein to an ocular region of the eye or intraarticular region in the body are described. The drug delivery systems may be used to treat a variety of ocular and medical conditions, including macular degeneration. Methods for using and making the drug delivery systems are also described. The drug delivery systems can be in the form of extruded filaments configured for placement in an ocular region such as the vitreous body or anterior chamber of the eye.

4 Claims, 5 Drawing Sheets

(56) References Cited

U.S. PATENT DOCUMENTS

| | | | |
|---|---|---|---|
| 8,206,707 | B2 | 6/2012 | Shima et al. |
| 2002/0111603 | A1 | 8/2002 | Cheikh |
| 2002/0169162 | A1 | 11/2002 | Smith et al. |
| 2004/0151753 | A1 | 8/2004 | Chen et al. |
| 2005/0244469 | A1 | 11/2005 | Whitcup et al. |
| 2005/0281861 | A1 | 12/2005 | Hughes et al. |
| 2006/0020044 | A1 | 1/2006 | Berlin |
| 2006/0182783 | A1 | 8/2006 | Hughes et al. |
| 2006/0233859 | A1 | 10/2006 | Whitcup et al. |
| 2006/0257452 | A1 | 11/2006 | Hughes et al. |
| 2007/0059336 | A1 | 3/2007 | Hughes et al. |
| 2008/0107694 | A1 | 5/2008 | Trogden et al. |
| 2008/0112822 | A1 | 5/2008 | Hughes et al. |
| 2008/0112923 | A1 | 5/2008 | Hughes et al. |
| 2008/0172014 | A1 | 7/2008 | Whitcup et al. |
| 2008/0241223 | A1 | 10/2008 | Nivaggioli et al. |
| 2008/0268051 | A1 | 10/2008 | Hughes et al. |
| 2009/0258924 | A1 | 10/2009 | Lyons et al. |
| 2010/0015158 | A1 | 1/2010 | Robinson et al. |
| 2010/0311808 | A1 | 12/2010 | Lyons et al. |
| 2011/0034448 | A1 | 2/2011 | Chang et al. |
| 2012/0045431 | A1 | 2/2012 | Lyons et al. |

FOREIGN PATENT DOCUMENTS

| | | |
|---|---|---|
| WO | WO 2006/041942 | 4/2006 |
| WO | WO 2006/122165 | 11/2006 |
| WO | WO 2007/089544 | 8/2007 |
| WO | WO 2008/134644 | 11/2008 |
| WO | WO 2010/009034 | 1/2010 |
| WO | 20110041642 A1 | 4/2011 |

OTHER PUBLICATIONS

Binz et al. (2004) "High affinity binders selected from designed ankyrin repeat protein libraries" *Nature Biotechnology* 22(5):575-582.

Board of Patent Appeals and Interferences, decision on Appeal in Ex parte Hughes et al., Appeal No. 2011-003859, U.S. Appl. No. 11/116,698, mailed Aug. 1, 2011.

Cook et al, "Age-related macular degeneration: diagnosis and management", British Medical Bulletin, vol. 85, Mar. 2008, pp. 127-149.

Eliaz et al. (2000) "Characterization of a polymeric PLGA-injectable implant delivery system for the controlled release of proteins" J Biomed Mater Res. 50(3):388-96.

Evonik Industries, Standard polymers product listing [online], 4 pages, [retrieved on Sep. 27, 2012] [retrieved from Evonik Industries website at URL: http://biomaterials.evonik.com/product/biomaterials/en/products-and-services/products/standard-polymers/Pages/default.aspx.

Ferrara et al, "Pituitary Follicular Cells Secrete a Novel Heparin-Binding Growth Factor Specific for Vascular Endothelial Cells", Biochemical and Biophysical Research Communications, vol. 161, No. 2, pp. 851-858, 1989.

Ghalanbor et al. (2010) "Improved lysozyme stability and release properties of poly(lactide-co-glycolide) implants prepared by hot-melt extrusion" *Pharmaceutical Res.* 27(2):371-379.

Giteau et al. (2008) "How to achieve sustained and complete protein release from PLGA-based microparticles?" *Int. J. Pharmaceutics* 350:14-26.

Hansen et al. (1995) "Attachment of antibodies to sterically stabilized liposomes: evaluation, comparison and optimization of coupling procedures" *Biochimica et Biophysica Acta* 1239:133-144.

Harper et al, "VEGF-A splicing: the key to anti-angiogenic therapeutics?", Nature Reviews/Cancer; Advance Online Publication, 2008, pp. 880-887.

Houck et al, "The Vascular Endothelial Growth Factor Family: Identification of a Fourth Molecular Species and Characterization of Alternative Splicing of RNA", Molecular Endocrinology, vol. 5, No. 12, 1991, pp. 1806-1814.

International Search Repor—PCT/US2009/050373, dated May 3, 2010.

Jain et al. (2000) "Comparison of various injectable protein-loaded biodegradable poly(lactide-co-glycolide) (PLGA) devices: in-situ-formed implant versus in-situ-formed microspheres versus isolated microspheres" Pharm Dev Technol. 5(2):201-7.

Jo et al, "Inhibition of Platelet-Derived Growth Factor B Signaling Enhances the Efficacy of Anti-Vascular Endothelial Growth Factor Therapy in Multiple Models of Ocular Neovascularization", American Journal of Pathology, vol. 168, No. 6, Jun. 2006, pp. 2036-2053.

Koch et al, "Signal transduction by vascular endothelial growth factor receptors", Biochem, J. (2011) 437, pp. 169-183.

Leung et al, "Vascular Endothelial Growth Factor Is a Secreted Angiogenic Mitogen", Science, 1989, vol. 246, pp. 1306-1309.

Löfblom et al. (2011) Non-immunoglobin based protein scaffolds *Curr. Opinion in Biotechnology* 22 :843-848.

Mordenti et al. (1999) "Intraocular pharmacokinetics and safety of a humanized monoclonal antibody in rabbits after intravitreal administration of a solution or a PLGA microsphere formulation" *Toxicological Sciences* 52:101-106.

Murata et al. (2008) "Anti-tumor effects of anti-VEGF siRNA encapsulated with PLGA microspheres in mice" *J. Controlled Release* 126:246-254.

Pan et al. (2011) "Comparison of long-acting bevacizumab formulations in the treatment of choroidal neovascularization in a rat model" *J Ocul Pharmacol Ther.* 27(3):219-24.

Rivers, Hongwen et al. (2011) "Sustained Delivery of Active Lysozyme with Selective PLGA Implants", Abstract T3017, 1 page, and Poster, AAPS Annual meeting Oct. 25, 2011.

Schlehuber and Skerra (2005) Lipocalins in drug discovery : from natural ligand-binding proteins to 'anticalins' *Drug Discovery Today* 10(1):23-33.

Schwach et al. (2003) "Biodegradable microparticles for sustained release of a new GnRH antagonist—part I: Screening commercial PLGA and formulation technologies" *Eur J Pharm Biopharm.* Nov.;56(3):327-36.

Stumpp et al. (2008) "DARPins: A new generation of protein therapeutics" *Drug Discovery Today* 13(15/16):695-701.

Tang et al, "Biodegradable and biocompatible thermosensitive polymer based injectable implant for controlled release of protein", International Journal of Pharmaceutics, 365 (2009), pp. 34-43.

U.S. Appl. No. 60/567,423, filed Apr. 30, 2004.
U.S. Appl. No. 60/679,771, filed May 10, 2005.
U.S. Appl. No. 60/721,600, filed Sep. 28, 2005.
U.S. Appl. No. 11/116,698, filed Apr. 27, 2005.
U.S. Appl. No. 11/364,687, filed Feb. 27, 2006.
U.S. Appl. No. 11/370,301, filed Mar. 8, 2006.
U.S. Appl. No. 11/416,929, filed May 2, 2006.
U.S. Appl. No. 11/931,769, filed Oct. 31, 2007.
U.S. Appl. No. 11/949,750, filed Dec. 3, 2007.
U.S. Appl. No. 11/949,751, filed Dec. 3, 2007.
U.S. Appl. No. 12/176,238, filed Jul. 18, 2008.

Yehoshua et al. (2011) "Current clinical trials in dry AMD and the definition of appropriate clinical outcome measures" *Seminars in Ophthalmology* 26(3):167-180.

International Searching Authority—PCT/US 2013/061803—International Filing Date Sep. 26, 2013.

Zhou, Shaobing et al., Synthesis and Characterization of Biodegradable Low Molecular Weight Aliphatic Polyesters and Their Use in Protein-Delivery Systems, Journal of Applied Polymer Science, 2004, pp. 1848-1856, vol. 91, Wiley Periodicals, Inc.

BIODEGRADABLE DRUG DELIVERY SYSTEMS FOR THE SUSTAINED RELEASE OF PROTEINS

CROSS-REFERENCE TO RELATED APPLICATIONS

This application claims the benefit of U.S. Provisional Patent Application Ser. No. 61/706,516, filed on Sep. 27, 2012, the entire disclosure of which is incorporated herein by reference.

FIELD

The present invention relates to biodegradable implants for the sustained release of a protein in a mammalian tissue. The implants are formulated to provide for the sustained delivery of a protein, such as an antibody, in a biologically active form in vivo for at least one month (30 days or more). The implants are useful for treating ocular conditions (including ocular diseases) affecting the anterior or posterior regions of the eye as well as medical conditions affecting regions and tissues throughout the body. Specific examples include implants configured for intraocular and intraarticular administration. Methods for making sustained-release, protein-containing implants are also described.

BACKGROUND

There is great interest in developing injectable, biocompatible compositions that can provide long-term release of a protein. It would be particularly advantageous to develop biocompatible and biodegradable compositions that release therapeutic levels of biologically active protein at a controlled rate for one, two, or three months or more.

Biodegradable compositions, such as intraocular implants, capable of delivering therapeutic levels of functional protein for extended periods could be extremely useful for the treatment of ocular disease, where the use of proteins, such as antibodies, typically requires frequent intraocular injection or high systemic dosing.

Aside from the discomfort and time associated with frequent injections, direct intraocular injection can involve certain risks to the patient, including retinal detachment, damage to the lens, and infection. Direct intraocular injection may also result in localized toxicity due to high pulsed concentrations of the protein drug at the lens and other intraocular tissues. Additionally, penetration of systemically administered proteins into the retina is severely restricted by the blood-retinal barriers (BRB).

Compounds are typically eliminated from the vitreous of the eye by diffusion to the retro-zonular space with clearance via the aqueous humor, or by trans-retinal elimination. Most high molecular weight compounds utilize the former pathway while lipophilic compounds and those with trans-retinal transport mechanisms will utilize the latter. Unfortunately, compounds that are eliminated across the retina have extremely short half-lives. Hence, for these compounds it is difficult to maintain therapeutic concentrations by direct intraocular injection. Frequent injection would be required. Even for macromolecules, such as proteins, that are cleared out via the aqueous humor, the vitreal half-life is short relative to the duration of therapy. Therefore, compounds such as LUCENTIS® must be dosed as frequently as once per month by intravitreal injection.

It would therefore be of great value to patients to obviate the need for frequent injections of proteins by developing biodegradable implants that can provide for the safe, effective, and long-term release of biologically active protein in a single dose while avoiding the high transient concentrations associated with pulsed dosing.

SUMMARY

Accordingly, some embodiments of the present invention provide for a biodegradable drug delivery system (DDS) that can release a therapeutically effective amount of biologically active protein in vivo for one month or more, two months or more, or three months or more (that is, 90 days or more).

The biodegradable drug delivery system may comprise, consist of, or consist essentially of a biodegradable polymer matrix and a protein associated with the biodegradable polymer matrix. Examples of drug delivery systems within the scope of the present invention include extruded filaments (i.e., an implant formed by an extrusion process) and compressed tablets.

For example, the biodegradable drug delivery system can be in the form of an extruded filament prepared by a single or double extrusion process. The extruded filament can be configured and sized for placement in an eye of a mammal, and more particularly in an ocular region of an eye. Such a filament may be referred to as an "intraocular implant," a "biodegradable intraocular implant," or more specifically as "an extruded biodegradable intraocular implant." Extruded filaments may also be configured for placement in an intraarticular region to treat a disease or medical condition thereof. Such a filament may be referred to as an "intraarticular implant." An extruded filament can be solid, semi-solid, or viscoelastic.

Accordingly, in one embodiment, the present invention provides for a biodegradable intraocular implant comprising or consisting of a biodegradable polymer matrix and a protein associated with the biodegradable polymer matrix, wherein the implant provides continuous release of the protein in a biologically active form for at least 30, 60, or 90 days after placement of the implant in an eye of a mammal. In one particular embodiment, the present invention provides for a biodegradable intraocular implant comprising a biodegradable polymer matrix and a protein associated with the biodegradable polymer matrix, wherein the implant provides continuous release of the protein in a biologically active form for more than 3 months after placement of the implant in an eye of a mammal. The protein can be encapsulated by and/or dispersed in the biodegradable polymer matrix. The protein can be uniformly or non-uniformly distributed in the polymer matrix. An implant may comprise a single protein or first and second proteins, such as first and second antibodies directed to first and second protein targets, whereby the antibodies are designed to bind to and block the activity of the first and second protein targets in vivo. One example is an implant comprising an antibody, DARPin (designed ankyrin repeat protein), or anticalin that specifically binds (in other words, is specific for) vascular endothelial growth factor (VEGF) or platelet derived growth factor (PDGF). For instance, an implant according to this invention can comprise an anti-VEGF or anti-PDGF antibody or both an anti-VEGF antibody and an anti-PDGF antibody.

Non-limiting examples of proteins that can be included in, and therefore delivered by an intraocular or intraarticular implant include monoclonal and polyclonal antibodies, bispecific antibodies, bispecific antibodies, antibody fragments, anticalins, DARPins, and enzymes. Other examples include glycoproteins and serum albumins. The monoclonal or polyclonal antibody can be used in its natural form as produced, for example, by a cell and may or may not contain post-translational modifications, or may be used in a chemically or enzymatically modified form produced subsequent to its isolation from a cell culture or other biological sample. The antibody may be chimeric. In specific embodiments, the antibody may be an IgA, IgD, IgE, IgG, or IgM. Useful antibody fragments include those generated by papain (e.g., the Fab fragment) or pepsin cleavage of an antibody. More generally, useful antibody fragments include Fab', F(ab)2, Fabc, and Fv fragments. The antibody fragments may either be produced by the modification of whole antibodies or those synthesized de novo using recombinant DNA methodologies, and further include "humanized" antibodies made by now conventional techniques. "Antibody fragments" comprise a portion of a full length antibody, generally the antigen binding or variable domain thereof.

Some embodiments of the present invention provide for a biodegradable implant comprising an anti-VEGF antibody or protein (i.e., an antibody or protein that specifically binds to vascular endothelial growth factor protein, or VEGF-A). Useful anti-VEGF antibodies include, but are not limited to, ranibizumab (LUCENTIS®) and bevacizumab (AVASTIN®). Useful anti-VEGF proteins include Aflibercept (Eylea®) (also known as VEGF TRAP), VEGF-binding DARPins, and VEGF-binding anticalins. VEGF Trap (Regeneron Pharmaceuticals, New York) is a fusion protein that contains portions of the extracellular domains of two different VEGF receptors connected to the Fc region (C-terminus) of a human antibody. In some embodiments the implant may comprise an antibody selected from the group consisting of anti-VEGF antibodies, anti-VEGF receptor antibodies, anti-PDGF (platelet derived growth factor) antibodies, anti-integrin antibodies, therapeutically effective fragments thereof, and combinations thereof.

In another embodiment, the present invention provides for an extruded biodegradable implant comprising an anti-TNF (tumor necrosis factor) antibody or protein. Useful anti-TNF antibodies include, but are not limited to, Adalimumab (HUMIRA®), Infliximab (REMICADE®), certolizumab pegol (CIMZIA®), and golimumab (SIMPONI®). Useful anti-TNF proteins include the fusion protein Etanercept (ENBREL®). Implants comprising anti-TNF proteins may be particularly useful for treating uveitis and Behcet's disease.

Other proteins for inclusion in an intraocular or intraarticular implant according to this invention include growth factors such as nerve growth factors, acid fibroblast growth factors, and basic fibroblast growth factors; neutrophic factors such as ciliary neurotrophic factor, brain-derived neurotrophic factor, and glial cell line-derived neurotrophic factor; cytokines such as interferon-gamma and interleukin-10; anti-proliferative compounds such as rituximab; and fibrinolysing protein such as tissue plasminogen activator. Therapeutic uses for such proteins may be generally known in the art.

Thus, a biodegradable intraocular or intraarticular implant according to this invention may comprise an antibody selected from the group consisting of anti-VEGF antibodies (antibodies that specifically bind to a VEGF), anti-PDGF antibodies, anti-VEGF receptor antibodies, anti-integrin antibodies, therapeutically effective fragments thereof, and combinations thereof.

Vascular endothelial growth factor A (VEGF-A, also referred to as VEGF), is a secreted mitogen specific for vascular endothelial cells that can stimulate endothelial cell growth in vitro and angiogenesis in vivo. VEGF-A can occur in different isoforms. All isoforms of VEGF-A, except VEGF-A$_{121}$, bind heparin. In humans the most abundant isoform of VEGF-A is a 165-amino acid polypeptide, VEGF-A$_{165}$. See, for example, Houck et al., Mol. Endocrin. 5:1806 (1991) and Leung et al., Science 246:1306 (1989).

Accordingly, some embodiments of the present invention provide for a biodegradable implant comprising a biodegradable polymer matrix and an antibody, DARPin, or anticalin that binds to VEGF-A$_{165}$. The same antibody, DARPin, or anticalin may recognize and bind all isoforms of VEGF-A since the antibody, DARPin, or anticalin may recognize an epitope present in all isoforms of VEGF-A. For example, the antibody, DARPin, or anticalin may recognize and specifically bind an epitope in the region of the VEGF-A receptor binding domains present in all isoforms of VEGF-A, including VEGF$_{121}$. Accordingly, a single anti-VEGF antibody (or DARPin or anticalin), in an implant of this invention may recognize and specifically bind all isoforms of VEGF-A. Antibodies, including monoclonal antibodies and humanized anti-VEGF antibodies, that bind to VEGF-A or VEGF receptor have been described. See, for example, U.S. Pat. Nos. 5,955,311 and 6,884,879. Bevacizumab is one example of a monoclonal antibody that specifically binds to and inhibits human VEGF-A. Inhibitory antibodies directed against PDGF have also been described. See, for example, WO 2003/025019.

Extended release biodegradable implants comprising a VEGF (vascular endothelial growth factor) or platelet-derived growth factor (PDGF) inhibitor or both, such as an antibody or combination of antibodies that specifically bind(s) VEGF and/or PDGF in vivo, may have particular utility for treating macular degeneration (including wet age-related macular degeneration), retinopathy, diabetic retinopathy, proliferative diabetic retinopathy, sickle cell retinopathy, retinopathy of prematurity, ischemic retinopathy, ocular neovascularization (abnormal growth of new blood vessels in the eye), choroidal neovascularization, neovascularization due to retinal vein occlusion, corneal neovascularization, diabetic retinal ischemia, and macular edema in a patient in need thereof.

In one embodiment, the invention provides for a biodegradable intraocular implant comprising a biodegradable polymer matrix and first and second antibodies, or a bispecific antibody, that specifically bind(s) VEGF and PDGF, respectively, wherein the implant provides continuous release of the first and second antibodies or bispecific antibody in a biologically active form for at least 30, 60, or 90 days after placement of the implant in an eye of a mammal. In one form, the antibodies or bispecific antibody are specific for vascular endothelial growth factor-A (VEGF-A) and platelet-derived growth factor-B (PDGF-B). These implants may be useful for treating ocular tumors, ocular neovascularization, choroidal neovascularization, and macular degeneration. By "PDGF-B" is meant a B chain polypeptide of PDGF.

The present implants are designed to maintain the biological activity of the antibody, such that when the antibody is released from the system it will specifically bind to its designated protein target. The binding of the antibody to the protein target may provide interference between the protein and its ligand or receptor, and thus the function mediated by a protein/receptor interaction can be inhibited or reduced by the antibody. Several methods for determining whether an antibody specifically binds to or is "immunoreactive with" a protein (polypeptide) target are known in the art. Immuno chemiluminescence metric assays (ICMA), enzyme-linked immunosorbent assays (ELISA) and radioimmunoassays (RIA) are some examples.

In some embodiments the present invention provides for an extruded biodegradable implant comprising a biodegradable polymer matrix and one or more monoclonal antibodies, bispecific antibodies, DARPins, anticalins, antibody fragments, recombinant polypeptides derived from an antibody variable region, or mixtures thereof, that interact(s) with (e.g., bind to and lessen or inhibit the activity of) VEGF or platelet-derived growth factor (PDFG) or both VEGF and PDFG. For example, the invention provides for an extruded biodegradable implant comprising a biodegradable polymer matrix and a bispecific antibody that specifically binds VEGF and PDFG, wherein the implant provides for continuous release of the antibody in a biologically active form for at least 90 days after placement of the implant in an eye of a mammal. In other embodiments an implant according to the invention may comprise a biodegradable polymer matrix and an antibody specific for the VEGF receptor.

Monoclonal antibodies useful in the present drug delivery formulations can be obtained using routine methods known to persons of ordinary skill in the art. Briefly, animals such as mice are injected with a desired target protein or portion thereof (the antigen), such as VEGF or VEGFR. The target protein is preferably coupled to a carrier protein. The animals are boosted with one or more target protein injections, and are hyperimmunized by an intravenous (IV) booster 3 days before fusion. Spleen cells from the mice are isolated and are fused by standard methods to myeloma cells. Hybridomas can be selected in standard hypoxanthine/aminopterin/thymine (HAT) medium, according to standard methods. Hybridomas secreting antibodies which recognize the target protein are identified, cultured, and subcloned using standard immunological techniques, and the antibody purified, for example, by affinity chromatography. In certain embodiments of the present delivery systems, an anti-VEGF or anti-VEGFR monoclonal antibody is obtained from ImClone Systems, Inc. (NY, N.Y.). For example, the present formulations may include an antibody available from ImClone Systems under the name IMC-18F1, or an antibody under the name of IMC-1121 Fab. Another anti-VEGF antibody fragment that may be used in the present drug formulations is ranibizumab, an Fab fragment that binds VEGF-A. Another anti-VEGF antibody useful in the present drug delivery systems is bevacizumab, a monoclonal antibody that binds VEGF-A.

In some embodiments the protein(s) in the drug delivery system (for example, the intraocular or intraarticular implant) may be at least 20, at least 30, at least 50, at least 100, at least 200, or at least 300 amino acids in length. In some embodiments the protein comprises three or more amino acids. In some instances the protein may be from 30 to 50 amino acids in length or from 100 to 500 amino acids in length. In some forms of the invention, the protein may have a molecular mass of less than 5 kilodaltons (kDa). In other forms the proteins may have a molecular mass of greater than 5 kDa, greater than 10 kDa, greater than 20 kDa, greater than 50 kDa, or greater than 100 kDa. In certain forms of the invention the protein may have a molecular mass of 10 to 30 kDa or 20 to 50 kDa. For example, the protein may have a molecular mass of 14 to 16 kDa, or 14 to 21 kDa. The protein may be linear, branched, or circular, and may be chemically synthesized (using, for example, solid phase synthesis) or naturally or recombinantly produced. The protein may be a fusion protein. The protein may be truncated relative to its naturally occurring form. The protein may comprise no more than a single amino acid chain or two or more amino acid chains. The two or more chains may be covalently or non-covalently associated with one another. For example, the amino acid chains may be associated through disulfide bonds, or the two or more chains may be associated with one another by non-covalent forces only. The protein may or may not contain synthetically or post-translationally modified amino acids. The proteins for use in the present implants may be produced recombinantly (by a mammalian or prokaryotic cell culture), synthetically (as, for example, by solid phase synthesis), or isolated from natural sources (e.g., mammalian or bacterial cell culture, plasma, serum, plant, fungus, or the like). One or more of the amino acids in a protein may be non-naturally occurring.

A biodegradable intraocular or intraarticular implant according to this invention may comprise from about 1.0% to about 50% protein by weight of the implant (i.e., % w/w), about 5% to about 30% protein by weight of the implant, about 5% to about 40% protein by weight of the implant, about 10% to about 25% protein by weight of the implant, or about 5%, 10%, 20%, or 30% protein by weight of the implant.

In addition to the protein and biodegradable polymer matrix, the implant may comprise one or more excipients, salts, buffering agents, preservatives, polyelectrolytes, or any combination thereof.

Useful excipients include carbohydrates such as trehalose (for example, trehalose, α,α-trehalose-dihydrate), inulin, and sucrose; surfactants such as polysorbate 20, polysorbate 80, and pluronic F127; polyethylene glycols such as polyethylene glycol 3350 (PEG 3350); amino acids such as glycine, aspartic acids, glutamic acids, arginine, lysine, and histidine; chelating agents such as ethylenediaminetetraacetic disodium salt dehydrate; polyhydric alcohols such as glycerol, sorbitol, and mannitol; cholesterol; albumins; cyclodextrins; dextrans; polyvinyl alcohol; glycerin; and zinc chloride, and combinations thereof. The excipient(s) may be present in the implant in an amount of from 0.01% by weight (w/w) to 30% (w/w), 0.01 to 20% by weight, or 0.01% to about 15% by weight.

Suitable water soluble buffering agents may include, without limitation, alkali and alkaline earth carbonates, phosphates, bicarbonates, citrates, borates, acetates, succinates and the like, such as sodium phosphate (e.g., monosodium phosphate ($NaH_2PO_4$), and disodium phosphate ($NaHPO_4$), sodium citrate, sodium borate, sodium acetate, sodium bicarbonate, sodium carbonate and the like. These agents are advantageously present in amounts sufficient to maintain a pH of the system of between 2 and 9 or, more specifically, between 4 and 8. The buffering agent may be present in the implant in an amount of 0.01% to 10% by weight (w/w), such as, for example, about 0.01% to 5% w/w.

Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in the implant in amounts of from 0.001% to about 5% by weight (w/w) such as, for example, 0.01% to about 2% w/w Suitable polyelectrolytes include polyarginine, polyhistidine, polylysine, protoamine, histones, polymyxin B sulfate, pollyallyamine, poly (ethyleneimine, DEAE-dextran, carrageenans, chondroitin sulphates, alginate sulphates, dextran sulphates, heparin, polystyrenesulphonate, polyvinylsulphate, and polyphosphate.

Suitable salts include NaCl, KCl, $MgCl_2$, and the like.

The biodegradable polymer matrix can comprise a poly (D,L-lactide), a poly(D,L-lactide-co-glycolide) (PLGA), or a combination thereof. In some embodiments, the matrix comprises a mixture of first and second PLGA copolymers. The first PLGA copolymer can have an ester end group and the second PLGA copolymer can have an acid end group. More specifically, the first PLGA copolymer can be RESOMER® RG752S and the second PLGA copolymer can be RESOMER® RG502H. In one specific embodiment, the weight to weight ratio of RG752S to RG502H in the drug delivery system (for example, in an extruded implant) is about 90 to 10. In another embodiment the first PLGA copolymer is RESOMER® RG753S and the second PLGA copolymer is RESOMER® RG502H. In a useful form, the weight to weight ratio of RG753S to RG502H in an extruded implant is about 90 to 10.

In some embodiments the implant may further comprise a resorbable polymer. A resorbable polymer is one that dissolves but does not degrade in vivo. Accordingly, a resorbable polymer is generally water soluble. One example of a resorbable polymer is polyethylene glycol 3350 (PEG 3350).

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymers which are included to form the matrix are desirably subject to enzymatic or hydrolytic instability. The degree of stability can be varied widely, depending upon the choice of monomer, whether a homopolymer or copolymer is employed, employing mixtures of polymers, and whether the polymer includes terminal acid groups.

The polymer matrix may comprise or consist of a biodegradable polymer or combination of first and second polymers. In addition to one or more polymers and in addition to the one or more proteins associated with the matrix, the polymer matrix may optionally further comprise one or more excipients, salts, buffering agents, preservatives, or polyelectrolytes, examples of which are described above.

Polylactide, or PLA, includes poly (D-lactide), poly (L-lactide), and poly(D,L-lactide), and may also be identified by CAS Number 26680-10-4, and may be represented by the formula:

Poly(lactide-co-glycolide) or PLGA, includes poly(D,L-lactide-co-glycolide), also identified by CAS Number 26780-50-7, and may be represented by a formula:

Thus, poly(D,L-lactide-co-glycolide) is a copolymer that comprises one or more blocks of D,L-lactide repeat units and one or more blocks of glycolide repeat units, where the size and number of the respective blocks may vary. The molar percent of each monomer (repeat unit) in a poly (lactide-co-glycolide) (PLGA) copolymer may be 0-100%, about 15-85%, about 25-75%, or about 35-65%. In some embodiments, the D,L-lactide to glycolide molar ratio may be about 50:50 or about 75:25.

The PLA and/or PLGA polymer included in the polymer matrix may comprise ester or free carboxylic acid end groups.

PLA and PLGA RESOMER® polymers are available from Evonik Industries AG, German.

RESOMER® R203H is a poly(D,L-lactide) having an acid end group and an inherent viscosity of 0.25-0.35 dl/g, as measured for a 0.1% w/v solution in chloroform ($CHCl_3$) at 25° C.

RESOMER® RG502 is a poly(D,L-lactide-co-glycolide) having an ester end group and an inherent viscosity of 0.16-0.24 dl/g (as measured for a 0.1% w/v solution in chloroform at 25° C.), and a D,L-lactide:glycolide ratio of about 50:50.

RESOMER® RG502H is a poly(D,L-lactide-co-glycolide) having an acid end group and an inherent viscosity of 0.16-0.24 dl/g (as measured for a 0.1% w/v solution in chloroform at 25° C.), and a D,L-lactide:glycolide ratio of about 50:50.

RESOMER® RG503H is a poly(D,L-lactide-co-glycolide) having an acid end group, an inherent viscosity of 0.32-0.44 dl/g (as measured for a 0.1% w/v solution in chloroform at 25° C.), and a D,L-lactide:glycolide ratio of about 50:50 (RESOMER® RG503H).

RESOMER® RG753S is a poly(D,L-lactide-co-glycolide) having an ester end group and an inherent viscosity of 0.32-0.44 dl/g (as measured for a 0.1% w/v solution in chloroform at 25° C.), and a D,L-lactide:glycolide ratio of about 75:25.

RESOMER® RG752S is a poly(D,L-lactide-co-glycolide) having an ester end group and an inherent viscosity of 0.16-0.24 dl/g (as measured for a 0.1% w/v solution in chloroform at 25° C.), and a D,L-lactide:glycolide ratio of about 75:25.

An implant according to the present invention may provide continuous release of a therapeutically effective amount of biologically active protein for at least about one, two, or three months after placement of the system in an ocular or intraarticular region. The protein, such as an antibody, may be released from the implant by diffusion, erosion, dissolution, or osmosis.

The amount of protein (such as an antibody) in a biodegradable implant for purposes of the present invention can be an amount effective for reducing one or more symptoms of an ocular or intraarticular condition. Such an amount may be between about 20 µg and about 500 µg of protein or more for example. Moreover, an implant (such as an extruded implant) will preferably release a therapeutically effective amount of the protein for a sustained period, which may be 30 to 90 days or more. A therapeutically effective amount of protein may be a release rate of about 0.5 µg of protein/day to about 4 µg of protein/day. In some cases, a therapeutically effective amount may be a release rate of about 0.5 µg protein/day to about 2 µg protein/day. For example, implants may provide a therapeutically effective amount of antibody when they release about 2 µg protein/day. Furthermore, an implant may provide a therapeutic effect for more than 3 months due not only to continuous release of protein for one, two, or three months or longer, but also due to the residual effect of the protein in the eye or tissue into which the implant has been placed.

The amount of protein continuously released over the at least about one, two, or three month period may be an amount therapeutically effective for treating an ocular condition (including an anterior or posterior ocular condition) or intraarticular disease or condition.

An extruded filament according to this invention can be sized and configured for placement in an ocular region of the eye, including the vitreous body, the anterior chamber, or the subconjunctival space. The extruded filament can be rod-shaped or non-cylindrical.

The biodegradable polymer matrix of a filament may comprise no more than one biodegradable polymer or may comprise a mixture of two or more biodegradable polymers. For example, the implant may comprise a mixture of first and second biodegradable polymers, wherein the first polymer is different than the second polymer. A polymer may differ from another polymer with regard to the end group, inherent viscosity, or repeating unit of the polymer, or any combination of thereof. One or more of the biodegradable polymers may have terminal acid groups. For example the first biodegradable polymer can be an acid-terminated polymer (have an acid end group), and the second biodegradable polymer can be an ester terminated polymer (have an ester end group). In another embodiment, the biodegradable polymer matrix comprises first, second, and third biodegradable polymers.

Accordingly, one example of a drug delivery system according to the present invention is an extruded filament (for example, an intraocular or intraarticular implant) comprising an antibody and a biodegradable polymer matrix, wherein the polymer matrix comprises a mixture of first and second biodegradable polymers, and wherein the filament releases a therapeutically effective amount of the antibody in biologically active form for at least about one month from the time the filament is placed in an ocular or intraarticular region. In particular embodiments thereof, the filament releases a therapeutically effective amount of biologically active antibody for at least about one, two, or at least about three months from the time the filament is placed in an ocular or intraarticular region.

Another example is an extruded filament comprising an antibody and a biodegradable polymer matrix, wherein the polymer matrix comprises no more than one biodegradable polymer, and wherein the filament releases a therapeutically effective amount of the antibody in biologically active form for at least about one month, or for at least about two, or three months from the time the filament is placed in an ocular or intraarticular region.

As previously explained, regardless of whether the extruded filament comprises one or more than one biodegradable polymer, the filament may, nevertheless, further comprise one or more excipients, salts, buffering agents, preservatives, or polyelectrolytes which may improve the stability and/or modulate the release rate of antibody from the filament. The release modulation may manifest in the form of a more linear rate of release and/or in a longer release period as compared to the same filament without the one or more excipients, salts, buffering agents, preservatives, or polyelectrolytes. Useful excipients, salts, buffering agents, preservatives, or polyelectrolytes have been previously set forth, above, and include polysorbate 20, trehalose, and sodium phosphate.

In filaments comprising a mixture of first and second biodegradable polymers, the first and second polymers can be independently selected from the group consisting of ester-terminated poly(D,L-lactide-co-glycolide) copolymers and acid-terminated poly(D,L-lactide-co-glycolide) copolymers. In a particular embodiment, the weight to weight ratio of ester-terminated to acid-terminated copolymers in the implant is 90:10.

In filaments comprising a single biodegradable polymer and no other biodegradable polymer, the single biodegradable polymer can be selected from the group consisting of ester-terminated poly(D,L-lactide-co-glycolide) copolymers (PLGA copolymers having ester end groups) and acid-terminated poly(D,L-lactide-co-glycolide) copolymers (PLGA copolymers having acid end groups).

In any of the foregoing embodiments, the ester-terminated and/or acid-terminated poly(D,L-lactide-co-glycolide) copolymer(s) may be independently selected from the group consisting of:
  i) a poly(D,L-lactide-co-glycolide) having an ester end group, an inherent viscosity of 0.16-0.24 dl/g (0.1% w/v in chloroform at 25° C.), and a D,L-lactide:glycolide ratio of about 75:25 (RESOMER® RG752S);
  ii) a poly(D,L-lactide-co-glycolide) having an ester end group, an inherent viscosity of 0.32-0.44 dl/g (0.1% w/v in chloroform at 25° C.), and a D,L-lactide:glycolide ratio of about 75:25 (RESOMER® RG753S);
  iii) a poly(D,L-lactide-co-glycolide) having an acid end group, an inherent viscosity of 0.16-0.24 dl/g (0.1% w/v in chloroform at 25° C.), and a D,L-lactide:glycolide ratio of about 50:50 (RESOMER® RG502H); and
  iv) a poly(D,L-lactide-co-glycolide) having an acid end group, an inherent viscosity of 0.32-0.44 dl/g (0.1% w/v in chloroform at 25° C.), and a D,L-lactide:glycolide ratio of about 50:50 (RESOMER® RG503H).

Some examples include the biodegradable implants of Formulation Nos. 1-9 listed and described in Table 1, below.

In one embodiment the invention provides for an extruded biodegradable filament (i.e., an extruded implant) comprising an antibody and a biodegradable polymer matrix, wherein the polymer matrix comprises RESOMER® RG753S and RESOMER® RG502H. In one form of this implant, the antibody is an anti-VEGF antibody.

In another embodiment the invention provides for an extruded biodegradable implant comprising an antibody, such as for example an anti-VEGF antibody, and a biodegradable polymer matrix, wherein the polymer matrix comprises RESOMER® RG752S and RESOMER® RG502H. In a particular form of this embodiment, the implant comprises RESOMER® RG752S and RESOMER® RG502H in a weight to weight ratio (RG752S to RG502H) of about 90 to 10, and the antibody is an anti-VEGF antibody. Examples include Formulation Nos. 3 and 5, described in Table 1, below.

In any of the foregoing embodiments, the filament may be configured for placement in an ocular or intraarticular region. That is the filament may be configured for use as an intraocular or intraarticular implant.

An extruded filament sized, configured, and suitable for placement in an ocular region (i.e., an intraocular implant) may be rod-shaped or non-cylindrical and from about 0.5 mm to about 10 mm in length. For example, the filament may be about 1 mm, 2 mm, 3 mm, 4 mm, 5 mm, 6 mm, or about 7 mm in length. The diameter may be from about 250 µm to about 1 mm, or less than about 500 µm. In one example a filament configured for placement in the vitreous body is about 1 to about 7 mm in length and about 0.5 to about 2 mm in diameter. In another example a filament configured for placement in the anterior chamber is about 0.5 to about 2 mm in length and about 50 µm to about 500 µm in diameter. These implants may also be suitable for administration to an intraarticular region to deliver a therapeutically effective amount of a protein to a patient in need thereof, such as for example a patient suffering from an inflammation or autoimmune disorder in a joint. The protein chosen for use in these implants will be one that is effective for reducing the inflammation or treating the autoimmune disorder.

The total weight of an intraocular or intraarticular implant can be from about 100 µg to about 5000 µg, about 1000 to about 2000 µg, or more than 5000 µg. For example, an extruded implant may weigh about 500 µg, about 1000 µg, about 2000 µg, or about 5000 µg.

Various techniques may be employed to produce biodegradable implants. Useful techniques include extrusion and compression methods. The preferred method for preparing protein-containing implants includes powder blending or milling of the protein powder with the polymers and, optionally, one or more excipients, salts, buffering agents, preservatives, or polyelectrolytes at the appropriate ratios. The protein powder is typically prepared by lyophilization or spray drying, in which excipients may be co-lyophilized or co-spray dried. The powder blend is subsequently extruded into filaments by a hot melt extruder such as a customized piston extruder or a twin screw extruder at appropriate extrusion temperature, extrusion rate, and extruder nozzle/screw size. A rod-shaped implant may be derived from filaments extruded from a nozzle and cut to desired size. The orifice of the nozzle may range from 200 to 440 µm in diameter.

The extrusion temperature can be from about 25° C. to about 150° C., or from about 60° C. to about 90° C., about 60° C. to about 100° C., or about 50° C. to about 80° C. An implant may be produced, for example, by bringing the temperature to about 60° C. to about 100° C. for protein/polymer mixing for a time period of about 5 minutes to 1 hour, 1 minute to about 30 minutes, or 5-20 minutes. For example, a time period may be about 10 to about 30 minutes, such as, for example, about 20 min. The implants are then extruded at a temperature of about 60° C. to about 90° C., or from about 60 to about 100° C.

The release rate of a protein from an implant may be empirically determined by formulating several implants with varying proportions of polymer, protein, and other components such as any of the excipients, salts, or buffers described herein. A USP approved method for dissolution or release test can be used to measure the rate of release (USP 23; NF 18 (1995) pp. 1790-1798). For example, using the infinite sink method, a weighed sample of the drug delivery device is added to a measured volume of a solution containing 0.9% NaCl in water (or other suitable release medium such as phosphate buffered saline (PBS)), where the solution volume will be such that the protein concentration after release is less than 20%, and preferably less than 5%, of saturation. The mixture is maintained at 37° C. and stirred slowly to ensure protein release. The amount of protein released into the release medium as a function of time may be followed by various methods known in the art, such as spectrophotometry, high performance (sometimes referred to as high pressure) liquid chromatography (HPLC), mass spectroscopy, etc. In the case of the present invention, the release of intact and biologically active antibody or other protein from an extruded implant can be monitored using size exclusion high performance liquid chromatography (SEC-HPLC) and enzyme-linked immunosorbent assay (ELISA).

The drug delivery systems, and therefore the biodegradable implants, described herein can be placed (or implanted) into an ocular region of an eye in a patient to treat a variety of ocular conditions, including macular degeneration (including wet age-related macular degeneration); ocular neovascularization (formation of new abnormal blood vessels in the eye), including but not limited to choroidal neovascularization, and iris neovascularization; acute macular neuroretinopathy; macular edema (including cystoid macular edema and diabetic macular edema); Behcet's disease; retinopathy, including diabetic retinopathy, and proliferative diabetic retinopathy; proliferative vitreoretinopathy; retinal arterial occlusive disease; central retinal vein occlusion; branch retinal vein occlusion; uveitic retinal disease; retinal detachment; an epiretinal membrane disorder; anterior ischemic optic neuropathy; non-retinopathy diabetic retinal dysfunction; retinitis pigmentosa; and glaucoma in a patient in need thereof.

The implants disclosed herein may also be placed in a joint to treat an intraarticular condition such osteoarthritis, rheumatoid arthritis, psoriatic arthritis, patellofemoral pain syndrome, joint pain, and joint inflammation in a patient in need thereof. Accordingly, in one embodiment the present invention provides for a method of treating an intraarticular condition (such as any of those named above) in a joint in a patient in need, the method comprising placing a biodegradable implant in the joint, wherein the implant comprises a protein effective for the treatment of the condition and a biodegradable polymer matrix, wherein the protein is associated with the matrix and wherein the implant reduces at least one symptom of the condition for 3 months or more after placement in the joint.

Definitions of the Invention

"Individual", "subject", or "patient" refers to a living human or non-human mammal, such as a primate, monkey, horse, dog, rabbit, rat, mouse, guinea pig, or pig. An individual or subject may be further classified as a patient, individual or subject in need of treatment of (suffering from) an ocular or medical condition.

As used herein, the term "ocular condition" refers to a disease or condition of one or more tissues, parts, or ocular regions of the eye that impairs the normal functioning of the eye. An ocular condition may be classified as an anterior ocular condition or posterior ocular condition.

An anterior ocular condition is a disease or condition affecting an anterior (front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber, the lens or the lens capsule and blood vessels and nerve which vascularize or innervate an anterior ocular region or site.

Examples of an anterior ocular condition include aphakia; pseudophakia; astigmatism; blepharospasm; cataract; conjunctival diseases; conjunctivitis; corneal diseases; corneal ulcer; dry eye syndrome; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye, that is to reduce intraocular pressure.

A posterior ocular condition is a disease or condition affecting a posterior ocular region or site in the eye such as choroid or sclera (in a position posterior to a plane through the posterior wall of the lens capsule), vitreous, vitreous chamber, retina, retinal pigmented epithelium, Bruch's membrane, optic nerve (the optic disc), and blood vessels and nerves which vascularize or innervate a posterior ocular region or site.

Examples of a posterior ocular condition include acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (neuroprotection).

The "eye" is the sense organ for sight, and includes the eyeball, or globe, the orbital sense organ that receives light and transmits visual information to the central nervous system. Broadly speaking the eye includes the eyeball and the ocular regions, tissues, and fluids which constitute the eyeball, the periocular muscles (such as the oblique and rectus muscles) and the portion of the optic nerve which is within or adjacent to the eyeball.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous body (sometimes referred to as the vitreous cavity), the choroid, the suprachoroidal space, the conjunctiva, the subconjunctival space, the sub-tenon space, the episcleral space, the intracorneal space, the epicorneal space, the sclera, the pars plana, surgically-induced avascular regions, the macula, and the retina.

The anterior chamber refers to the space inside the eye between the iris and the innermost corneal surface (endothelium).

The posterior chamber refers to the space inside the eye between the back of the iris and the front face of the vitreous. The posterior chamber includes the space between the lens and the ciliary process, which produces the aqueous humor that nourishes the cornea, iris, and lens and maintains intraocular pressure.

An "intravitreal" implant is one that is sized, configured, and formulated for placement in the vitreous body of the eye.

As used herein, an "intraocular implant" refers to a device or element that is configured to be placed in an ocular region of the eye. Examples include extruded filaments, comprising a biodegradable polymer matrix and a protein associated with the polymer matrix, and cut to a length suitable for placement in an eye. Intraocular implants are generally biocompatible with physiological conditions of an eye and do not cause adverse reactions in the eye. In certain forms of the present invention, an intraocular implant may be configured for placement in the vitreous, anterior chamber, subconjunctival space or sub-tenon space. Intraocular implants are generally biocompatible with physiological conditions of an eye and do not cause adverse side effects. Intraocular implants may be placed in an eye without disrupting vision of the eye. Implants can be biodegradable and may be produced by an extrusion process, as described herein. Implants produced by an extrusion process and comprising a protein and a biodegradable polymer matrix are one example of a drug delivery system within the scope of the present invention.

The term "biocompatible" means compatible with living tissue or a living system. Biocompatible implants and polymers produce few or no toxic effects, are not injurious, or physiologically reactive and do not cause an immunological reaction.

As used herein, "associated with a biodegradable polymer matrix" means mixed with, dissolved and/or dispersed within, encapsulated by, or coupled to.

As used herein, the term "medical condition" refers to a condition or disease of a tissue or structure of the body that impair(s) the normal function or use of the tissue or structure. Medical conditions include ocular and intraarticular conditions.

Examples of intraarticular conditions include rheumatoid arthritis, inflammation and pain associated with inflammation of a joint. The intraarticular condition may impair and thereby restrict a subject's mobility. A biodegradable drug delivery system of the type described herein may be useful for delivering an effective amount of a therapeutically useful protein to the joint thereby reducing inflammation and relieving pain in a subject in need.

The term "intraarticular" means situated within, occurring within, or administered by entry into a joint.

An "intraarticular region" refers to a joint, such as a knee, elbow, shoulder, finger, toe, or hip joint. Intraarticular regions include joints in the wrist and vertebral column in the neck and back.

A "joint" as used herein refers to the point of contact between two or more bones of an animal or human skeleton with the parts that surround and support it. Examples of joints include without limitation the knee joint, toe and finger joints, wrist, ankle, hip, shoulder, back (vertebrae and vertebral discs), and elbow.

The term "biodegradable polymer" refers to a polymer or polymers which degrade in vivo, and wherein erosion of the polymer or polymers over time occurs concurrent with or subsequent to release of the therapeutic agent. The terms "biodegradable" and "bioerodible" are equivalent and are used interchangeably herein. A biodegradable polymer may be a homopolymer, a copolymer, or a polymer comprising more than two different polymeric units.

The term "therapeutically effective amount" as used herein, refers to the level or amount of agent needed to treat an ocular or medical condition, or reduce or prevent ocular injury or damage without causing significant negative or adverse side effects to the eye or a region of the eye or body part to which the agent is administered. In view of the above, a therapeutically effective amount of a protein, such as an antibody, is an amount that is effective in reducing at least one symptom of a medical condition such as an ocular or intraarticular condition. By reducing one or more symptoms of an ocular condition, a therapeutically effective amount of a protein may improve the optical quality and visual performance of an eye in an individual suffering from the ocular condition. By reducing one or more symptoms of a medical condition, a therapeutically effective amount of a protein may improve the physical health, well being, and/or mobility of the subject. A protein that reduces or resolves at least one symptom of a medical condition is a therapeutic protein, or a protein therapeutically effective for the treatment the medical condition.

As used herein, the terms "treating" and "treats" refers to the reduction or resolution of at least one symptom of an ocular or medical condition. Reduction or resolution of a symptom may be observed or experienced as an improvement in vision, and/or as a reduction in swelling, pain, or redness. "Treating" includes any beneficial or medicinal effect in the eye or body tissue of an individual produced by administration of a drug delivery system (for example, a biodegradable implant) as described herein, which effect can be a reduction of one or more symptoms of the ocular or medical condition and/or as an improvement in the well being, visual performance and/or optical quality of the eye(s) in the individual. A reduction of one or more symptoms includes but is not limited to a reduction in ocular pain, joint pain, inflammation, or discomfort. The symptom(s) positively affected (i.e., reduced) by the treatment, will depend on the particular condition.

A "bispecific monoclonal antibody (BsMAb)" is an artificial protein that is composed of fragments of two different monoclonal antibodies and consequently is capable of binding to two different types of antigen.

A "bispecific antibody" is an antibody capable of simultaneously binding two different targets, such as two different proteins.

"Cumulative release profile" means the cumulative total percent of an active agent (such as a therapeutic protein) released from an implant into an ocular region or site in vivo over time or into a specific release medium in vitro over time.

DETAILED DESCRIPTION OF THE INVENTION

The invention can be further understood with reference to the following description and examples together with the appended drawings.

In certain forms of the present invention the drug delivery system is in the form of a biodegradable intraocular or intraarticular implant. The implant may be produced by an extrusion process. Generally, implants are solid or semi-solid. An "implant" is a drug delivery device which is considerably larger than a microsphere. The biodegradable implant will generally comprise a protein associated with a biodegradable polymer matrix. The matrix may comprise two or more biodegradable polymers and/or two or more structurally distinct proteins. The implant is preferably configured for implantation into ocular region of the eye or intraarticular space of the body, such as a finger, elbow, or knee joint, and formulated to provide for the release of a therapeutically effective amount of protein in biologically active form for at least about 1, 2, 3, or 6 months. In some embodiments the implant may release biologically active protein continuously for 2 months or more, or for 3 months or more.

The "biologically active form" of a protein is the form having the size and tertiary structure normally expected for the protein under non-denaturing conditions and that is able, therefore, to perform the biochemical activity normally expected of the protein. In the case of DARPins, anticalins, and antibodies the biologically active form is the form that specifically binds (is immunoreactive with) the expected antigen. Examples of antigens include proteins (including enzymes). The expected antibody binding specificity can be based on knowledge of the antigen used to initially generate the antibody and/or to purify the antibody, or on the identity of the antigen used (e.g., in an assay such as an ELISA) to detect the presence and/or measure the amount (titer) of the antibody in a sample prior to its incorporation into a drug delivery system (such as extruded implant). In the case of enzymes, the biologically active form is the form that catalyzes the chemical reaction it would be expected to catalyze in vitro or in vivo prior to its incorporation into a drug delivery system (such as an extruded implant). The biological activity of an antibody in vivo or in vitro may be observed and/or measured by the reduction in activity of a target protein. For example, the specific binding of an antibody, DARPin, or anticalin to a protein target may provide interference between the protein target and its ligand or receptor, and thus the function mediated by a protein/receptor interaction can be inhibited or reduced. Accordingly, interference of a particular function or activity in a cell system (for example, a cell culture) or tissue in vitro or in vivo may serve as one indication of the biological activity of an antibody administered to that cell system or tissue. Additionally, several other methods for determining the specific binding of an antibody are known in the art. Immunochemiluminescence metric assays (ICMA), enzyme-linked immunosorbent assays (ELISA), and radioimmunoassays (RIA) are some examples.

As described previously, "a biodegradable polymer matrix" may comprise no more than one biodegradable polymer or may comprise a combination of two, three, or more biodegradable polymers. The biodegradable polymer matrix, and therefore an implant, may optionally further comprise an excipient, salt, buffering agent, preservative, or polyelectrolyte, which may modulate the release of the protein from the biodegradable polymer matrix. The protein may be associated with or dispersed within the biodegradable polymer matrix.

In addition to a biodegradable polymer or combination of polymers thereof, a drug delivery system, such as an extruded implant, may optionally further comprise a resorbable polymer such as PEG 3350. The amount of PEG 3350 in an implant may vary, for example, from 1% to 20% by weight of the total weight of the implant (% w/w).

A biodegradable drug delivery system, as described herein, may be in the form of an extruded filament, which may be sized (for example, cut to a length suitable) for placement (implantation) in an ocular region of the eye, such as the anterior chamber, subtenon space, vitreous body, or subconjunctival space.

It may be understood that the polymeric component of the present systems is associated with the protein so that the release of the protein into the eye or other tissue in the body is by one or more of diffusion, erosion, dissolution, and osmosis. As discussed herein, the polymeric matrix of a drug delivery system may release protein at a rate effective to sustain release of a therapeutically effective amount of protein (and therefore protein in biologically active form) for more than one month, two months, three months, or four months after insertion into the eye. The release of protein from an implant comprising a biodegradable polymer matrix may include an initial burst of release followed by a gradual increase in the amount of the protein released, or the release may include an initial delay in release of the protein followed by an increase in release. When the system is substantially completely degraded, the percent of the protein that has been released is about one hundred. Burst refers to the amount of drug (for example protein) released during the first day following placement of an implant in a mammal or liquid medium (such as an aqueous buffer or saline solution). Delay refers to a period in which little or no drug is released relative to the rate of release during any other period. A burst of drug release may be useful in certain ocular conditions such as choroidal neovascularization (CNV), where there may be an excessive amount of VEGF that needs to be blocked or effectively inhibited by the drug. A delay in release may be useful as a means to prolong the duration of release.

The polymeric drug delivery systems used in the present method may be monolithic, i.e. having the protein homogenously distributed throughout the polymeric matrix.

Prior to use in a subject, an implant may be sterilized with a suitable dose of gamma or beta-radiation. Preferably, the sterilization method does not reduce the activity or biological or therapeutic activity of the therapeutic agents of the present systems. As an example, the implant can be sterilized by 5-25 kGy of gamma or beta-irradiation. In some instances, 10 to 15 kGy of gamma or beta-irradiation may be used.

One embodiment of the present invention is a method for treating an ocular condition in a patient in need thereof, the method comprising placing a biodegradable intraocular implant in an eye of the patient, wherein the implant comprises a biodegradable polymer matrix and a protein effective for the treatment of the ocular condition. The implant can be an extruded filament and the protein can be associated with the biodegradable polymer matrix. The implant may be placed in the anterior chamber, vitreous body, subconjunctival space, or subtenon space of the eye to thereby treat the ocular condition for an extended period, such as for one, two, three, or four months or more.

Another embodiment of the present invention is a method for treating an intraarticular condition in a patient in need thereof, the method comprising placing a biodegradable intraocular implant in a joint of the patient, wherein the implant comprises a biodegradable polymer matrix and a protein effective for the treatment of the intraarticular condition. The implant can be an extruded filament and the protein can be associated with the biodegradable polymer matrix.

The implants of the present invention may be inserted into an ocular region of the eye or intraarticular region of the body by a variety of methods, including placement by forceps, syringe (equipped with a cannula or needle), trocar, or other suitable device. Suitable devices (apparatus) include those disclosed in U.S. patent Publication No. 2004/0054374 and U.S. Pat. No. 6,899,717.

A syringe apparatus including an appropriately sized needle, for example, a 22 gauge needle, a 27 gauge needle or a 30 gauge needle, can be effectively used to inject an implant into an eye of a human or animal. Repeat injections are often not necessary due to the extended release of the protein from the implants. This may be of particular value in the treatment of age-related macular degeneration where frequent injections are sometimes necessary to maintain therapeutically effective levels of the protein.

The present invention includes, but is not limited to, the following embodiments (1-24):

1. An extruded biodegradable intraocular implant comprising a biodegradable polymer matrix and a protein associated with the biodegradable polymer matrix, wherein the biodegradable polymer matrix comprises a poly(D,L-lactide-co-glycolide), and wherein the implant provides continuous release of the protein in a biologically active form for at least 30 days after placement of the implant in an eye of a mammal.

2. The implant of 1, wherein the biodegradable polymer matrix comprises a first poly(D,L-lactide-co-glycolide) and a second poly(D,L-lactide-co-glycolide), the first poly(D,L-lactide-co-glycolide) having an ester end group and a D,L-lactide:glycolide ratio of about 75:25, and the second poly(D,L-lactide-co-glycolide) having an acid end group and a D,L-lactide:glycolide ratio of about 50:50, wherein the implant provides continuous release of the protein in a biologically active form for about 90 days after placement of the implant in an eye of a mammal.

3. The implant of 2, wherein the weight to weight ratio of first poly(D,L-lactide-co-glycolide) to second poly(D,L-lactide-co-glycolide) is about 90:10.

4. An implant according to any of 1-3, wherein the protein is therapeutically effective for the treatment of an ocular condition.

5. An implant according to 4, wherein the protein is therapeutically effective for reducing at least one symptom of an ocular condition selected from the group consisting of ocular neovascularization, choroidal neovascularization, macular degeneration, and macular edema.

6. An implant according to 5, wherein the protein is an antibody, antibody fragment, bispecific antibody, anticalin, or DARPin.

7. An implant according to 6, wherein the protein is an antibody, antibody fragment, DARPin, or anticalin that binds vascular endothelial growth factor (VEGF) or platelet-derived growth factor (PDGF).

8. The implant of 7, wherein the protein is an anti-VEGF antibody.

9. An implant according to 6, wherein the protein is a bispecific antibody that binds vascular endothelial growth factor (VEGF) and platelet-derived growth factor (PDGF).

10. An implant according to 7, wherein the protein is an antibody that binds vascular endothelial growth factor (VEGF) or platelet-derived growth factor (PDGF), and wherein the implant effectively inhibits or reduces the activity of VEGF or PDGF in vivo in an eye of a mammal for at least 4 weeks after placement of the implant in an eye of a mammal.

11. An implant according to 10, wherein the protein is an antibody that binds VEGF (an anti-VEGF antibody), and wherein the implant provides continuous release of the anti-VEGF antibody in a biologically active form for about 90 days after placement of the implant in an eye of a mammal.

12. An implant according to any of 1-10, wherein the biodegradable polymer matrix comprises
    a) a poly(D,L-lactide-co-glycolide) having an ester end group, an inherent viscosity of 0.16-0.24 dl/g (0.1% in chloroform at 25° C.), and a D,L-lactide:glycolide ratio of about 75:25 (RESOMER® RG752S);
    b) a poly(D,L-lactide-co-glycolide) having an ester end group, an inherent viscosity of 0.32-0.44 dl/g (0.1% in chloroform at 25° C.), and a D,L-lactide:glycolide ratio of about 75:25 (RESOMER® RG753S);
    c) a poly(D,L-lactide-co-glycolide) having an acid end group, an inherent viscosity of 0.16-0.24 dl/g (0.1% in chloroform at 25° C.), and a D,L-lactide:glycolide ratio of about 50:50 (RESOMER® RG502H);
    d) a poly(D,L-lactide-co-glycolide) having an acid end group, an inherent viscosity of 0.32-0.44 dl/g (0.1% in chloroform at 25° C.), and a D,L-lactide:glycolide ratio of about 50:50 (RESOMER® RG503H); or
    e) a combination thereof 13. An implant according to 12, wherein the implant further comprises trehalose, sodium phosphate, polysorbate 20, or a combination thereof.

14. An implant according to 13 the implant comprising about 82.5% by weight of a poly(D,L-lactide-co-glycolide) having an acid end group, an inherent viscosity of 0.32-0.44 dl/g (0.1% in chloroform at 25° C.), and a D,L-lactide:glycolide ratio of about 50:50 (RESOMER® RG503H); about 10% by weight antibody, DARPin, or anticalin; about 6% by weight trehalose; about 0.1% by weight polysorbate 20; and about 1.4% by weight sodium phosphate.

15. An implant according to 13, the implant comprising about 8.8% by weight of a poly(D,L-lactide-co-glycolide) having an acid end group, an inherent viscosity of 0.16-0.24 dl/g (0.1% in chloroform at 25° C.), and a D,L-lactide:glycolide ratio of about 50:50 (RESOMER® RG502H); about 79.7% by weight of a poly(D,L-lactide-co-glycolide) having an ester end group, an inherent viscosity of 0.16-0.24 dl/g (0.1% in chloroform at 25° C.), and a D,L-lactide:glycolide ratio of about 75:25 (RESOMER® RG752S); about 10% by weight antibody, DARPin, or anticalin; about 0.1% by weight polysorbate 20; and about 1.4% by weight sodium phosphate.

16. An implant according to any of 1-15, wherein the implant is extruded at a temperature between 60° C. and 90° C.

17. An apparatus for injecting an intraocular implant into the eye of a mammal, said apparatus comprising i) an elongate housing having a longitudinal axis; and ii) a cannula extending longitudinally from the housing, said cannula having a proximal end, a distal sharp end, and a lumen extending therethrough, the cannula further comprising an implant as defined by any of 1-16 above, wherein the implant is located within the lumen of the cannula.

18. A method for treating an ocular condition in an eye of a mammal in need thereof, the method comprising placing in the eye of the mammal an implant according to any of 1-16, thereby treating the ocular condition.

19. The method of 18, wherein the ocular condition is ocular neovascularization, choroidal neovascularization, macular degeneration, or macular edema.

20. The method of 19, wherein the implant is placed in the vitreous body of the eye.

21. The method of 20, wherein the mammal is a human.

22. The method of 21, wherein the implant effectively treats the ocular condition for at least about 4 weeks after the implant is placed in the eye.

23. The method of 22, wherein the implant effectively treats the ocular condition for about 90 days after the implant is placed in the eye.

24. A method for making a biodegradable intraocular implant that provides continuous release of a protein in a biologically active form for at least 30, 60, or 90 days after placement of the implant in an eye of a mammal, the method comprising:
    a) providing a dry powder comprising one or more proteins and, optionally, one or more excipients, salts, buffering agents, preservatives, polyelectrolytes, or combination thereof;
    b) blending the dry powder with one or more poly(D,L-lactide-co-glycolide) copolymers to form a mixture;
    c) extruding the mixture at a temperature between 60° C. and 90° C. to form a filament;
    d) cutting the filament to form an implant 0.5 to 10 mm in length suitable for placement in an ocular region of an eye.

Example 1

Formulations

Monoclonal antibodies were incorporated into PLGA or PLA implants by extrusion. The composition of AVASTIN®, a commercially available monoclonal antibody, is 25 mg/ml bevacizumab, 60 mg/ml α,α trehalose-dihydrate, 51 mM sodium phosphate pH 6.2, and 0.04% polysorbate 20. Buffer exchange was performed with a Zeba desalt spin column to reformulate the AVASTIN® composition with various types and amounts of carbohydrates, salts, and surfactants. The reformulated composition was then lyophilized to form a powder. If desired, additional excipients such as solubility enhancing components, release modulators, and preservatives may be added and co-lyophilized with the protein composition. The lyophilized powder was blended with polymers and excipients at the appropriate ratios with a Turbula Shaker. The components may be milled individually or collectively with a Retsch M200. The powder blend was then extruded into filaments with different diameter dimensions and subsequently cut into implants with a range of lengths. Several PLGA/PLA-monoclonal antibody implants were fabricated as described in the examples below. Monoclonal antibody release from implants was assessed in vitro.

Implants were placed into vials containing release medium (PBS with 0.01% sodium azide) and shaken at 37° C. At the appropriate time points a sample was taken from the release medium for analysis and the medium totally replaced with fresh medium to maintain sink conditions. Intact antibody in the sample was assayed by SEC-HPLC and the cumulative percent release of drug from the implant noted as a function of time. Activity of the antibody was determined by ELISA.

Example 2

Manufacturing and Testing of Implants Containing a Monoclonal Antibody and a Biodegradable Polymer The full-length monoclonal antibody, bevacizumab, was reformulated from its original composition (AVASTIN®) with a Zeba desalt spin column (Thermo scientific), as described above in Example 1. The relative amounts of excipients and buffering agent in the AVASTIN® formulation were varied within a range of concentrations for sodium phosphate (0 to 51 mM, comprising monosodium and disodium phosphate for a pH prior to lyophilization of about 6-7), α,α trehalose-dihydrate (0 to 60 mg/ml), and polysorbate 20 (0 to 0.04%) and colyophilized with the bevacizumab antibody. If desired, additional excipients such as PEG 3350 (0 to 10 mg/ml) may be added and co-lyophilized. The lyophilized powder was obtained on a FTS Lyostar using a lyophilization cycle suitable for proteins.

The moisture content of the dry powder was measured to range from 3-6% by thermogravimetric analysis (TGA) and the purity of the antibody was determined to range from 70-100% by size exclusion chromatography-HPLC (SEC-HPLC).

A TSKgel G3000SW×1 (7.8 mm×30 cm) column was used for separation. The SEC-HPLC was run isocratic at a flow rate of 0.5 ml/min for a run time of 30 minutes. The detector was set to a wavelength of 280 nm.

Different polymer compositions were obtained from Boehringer Ingelheim Corp including RESOMER® Products RG502H, RG503H, RG504H, RG502, RG503, RG504, RG752S, RG753S, RG755S, R203S, and R203H. Polymer components, additional excipients, if any, and lyophilized powder were blended in appropriate ratios using a Turbula shaker type T2F (Glenn Mills) at 96 rpm for 10 minutes (twice) or milled using a Retsch model MM200 at 20 cpm for 10 minutes (twice). The powder mixture was compacted into a stainless steel barrel with a modified pneumatic drive powder compactor (Janesville Tool) set to 50 psi. The powder mixture was extruded using a customized piston extruder. The process parameters were selected based on the composition of the formulation and the desired diameter dimension. The nozzle diameter ranged from 400 to 480 μm. The extrusion temperature ranged from 60 to 90° C. The system was allowed to equilibrate for 20 minutes prior to extrusion at a rate of 0.0025 in/min. The first 2-4 inches of the extrudate was discarded. Subsequently, 3-5 inch pieces were cut into a centrifuge tube. Samples were labeled and stored in a sealed foil pouch with desiccant.

Six 5-6 mm length samples (1 to 1.5 mg) were cut from each formulation. Samples were weighed and placed into 4 mL glass vial. Two milliliters of release medium (Dulbecco's phosphate buffer saline with 0.2 mg/ml sodium azide) was added to each vial. Each vial was parafilmed and placed into a shaking water bath set at 37° C. and 50 rpm. At each time point, a sample was taken from the release medium for analysis, and the medium was fully replaced with 2 mL of fresh medium. Samples were analyzed using a Waters 2690 Separation Module and a Waters 2487 Dual Wavelength Absorbance Detector. A TSK gel G3000SW×1 (7.8 mm×30 cm) column can be used for separation. The release rates can be determined by calculating the amount of antibody being released in a given volume of medium over time. Select samples were analyzed for activity by an enzyme-linked immunosorbent assay (ELISA) using a recombinant human VEGF-A as the capture antibody and an anti-human Fc/HRP as the detection antibody. Table 1 lists examples of antibody-containing intraocular implants (extruded filaments) produced according to this process. The RESOMER® PLGA and PLA polymer(s) included in each formulation are identified by polymer number at the top of the table. The rate and duration of antibody release from these implants in vitro is shown in FIGS. 1-6 and 8 and described below.

TABLE 1

Protein-containing biodegradable implants (extruded filaments)

| Formulation No. | Protein | Excipient (s) | Composition (% w/w) | | | | |
|---|---|---|---|---|---|---|---|
| | | | RG503H | RG502H | RG752S | RG753S | R203H |
| 1 | 10 bevacizumab | 6 Trehalose<br>0.1 Polysorbate 20<br>1.4 Sodium phosphate | 82.5 | | | | |
| 2 | 10 bevacizumab | 6 Trehalose<br>0.1 Polysorbate 20<br>1.4 Sodium phosphate | | 8.2 | | 74.3 | |

TABLE 1-continued

Protein-containing biodegradable implants (extruded filaments)

| Formulation No. | Protein | Excipient (s) | Composition (% w/w) | | | | |
|---|---|---|---|---|---|---|---|
| | | | RG503H | RG502H | RG752S | RG753S | R203H |
| 3 | 10 bevacizumab | 0.1 Polysorbate 20<br>1.4 Sodium phosphate | | 8.8 | 79.7 | | |
| 4 | 5 bevacizumab | 12 Trehalose<br>0.1 Polysorbate 20<br>1.4 Sodium phosphate | | | | 81.5 | |
| 5 | 5 bevacizumab | 12 Trehalose<br>0.1 Polysorbate 20<br>1.4 Sodium phosphate | | 8.1 | 73.4 | | |
| 6 | 5 bevacizumab | 12 Trehalose<br>0.1 Polysorbate 20<br>1.4 Sodium phosphate | | | 40.7 | 40.8 | |
| 7 | 5 bevacizumab | 8 Trehalose<br>0.1 Polysorbate20<br>1.4 Sodium phosphate | | | | 85.5 | |
| 8 | 5 bevacizumab | 4 Trehalose<br>0.1 Polysorbate 20<br>1.4 Sodium phosphate | | | | 89.5 | |
| 9 | 20 bevacizumab | 6 Trehalose<br>0.1 Polysorbate 20<br>1.4 Sodium phosphate | 72.5 | | | | |
| 10 | 5 bevacizumab | 12 Trehalose<br>0.1 Polysorbate 20<br>1.4 Sodium phosphate | | | | | 81.5 |

Figure 1:
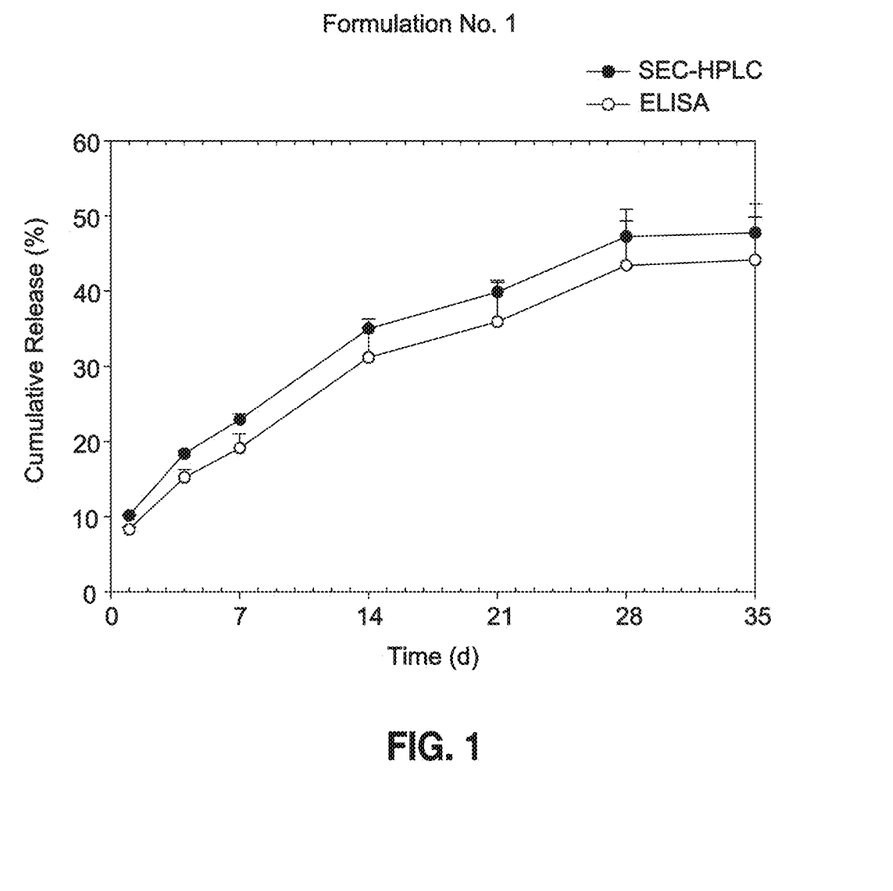
FIG. 1 shows the in vitro release of bevacizumab from a PLGA-bevacizumab implant (Formulation No. 1) (0.53 mm×5 mm), showing comparable profiles by SEC-HPLC and ELISA indicating that the binding activity is retained after one month of incubation in the release medium.

FIG. 1 displays the in vitro release of bevacizumab from a PLGA-bevacizumab implant comprising 82.5% by weight RG503H, 10% by weight bevacizumab, 6% by weight trehalose, 1.4% by weight sodium phosphate, and 0.1% by weight polysorbate 20 (Formulation No. 1). The graph shows that about 10% of the monoclonal antibody is released from the polymeric implant within the first day. A relatively constant rate of release is observed for the first 28 days, with a cumulative release of around 45% drug by day 28. By 35 days, a minor amount of intact antibody is released. Importantly, comparable release profiles are observed by SEC-HPLC and ELISA, illustrating that the monoclonal antibody retained its biological activity after incorporation into and release from the biodegradable polymer.

Figure 2:
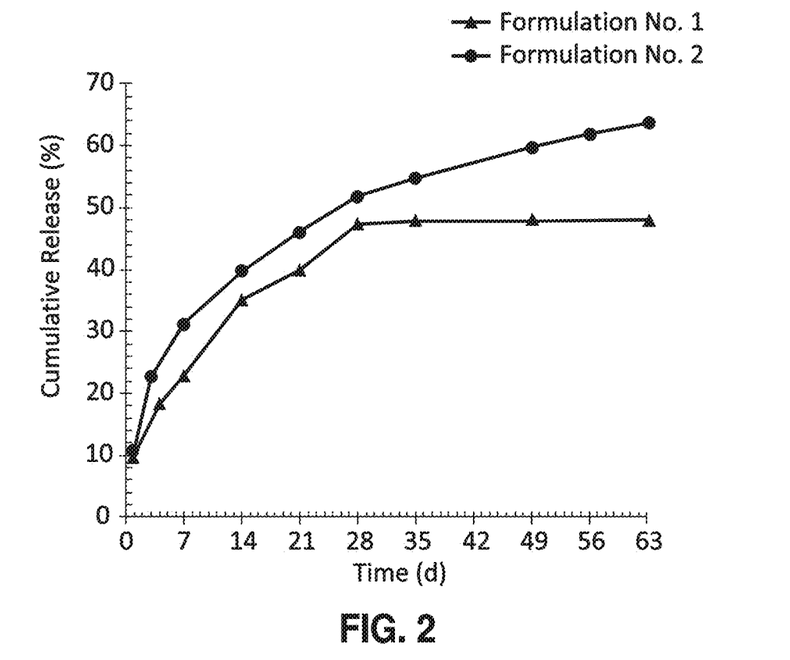
FIG. 2 shows the in vitro release (SEC-HPLC) of bevacizumab from two different PLGA-bevacizumab implants (Formulation Nos. 1 and 2) showing an increase in sustained duration from 1 month to 2 months by altering the polymer composition.

FIG. 2 illustrates the ability to increase the duration of drug release from PLGA implants by the selection of the polymer. By blending RG753S and RG502H at a ratio of 90 to 10 (Formulation No. 2), the PLGA-bevacizumab implant shows an increased duration of release, from 1 month to 2 months.

Figure 3:
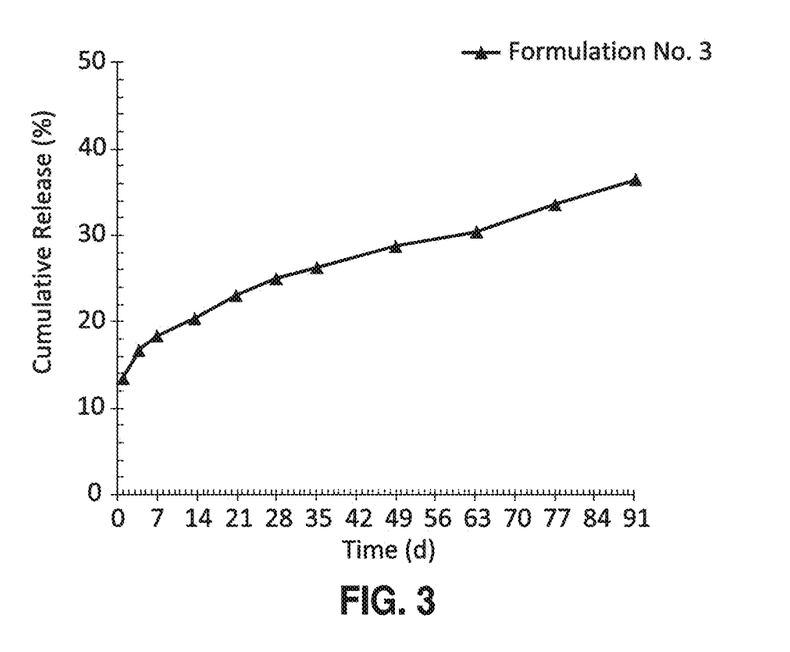
FIG. 3 shows the in vitro release (SEC-HPLC) of bevacizumab from a PLGA-bevacizumab implant (Formulation No. 3) showing an increase in sustained duration to 3 months by altering the polymer composition.

FIG. 3 illustrates the ability to increase the sustained duration to at least 3 months (about 90 days) by altering the formulation composition. In this example, the trehalose excipient is removed and the polymer is a blend of RG752S and RG502H at a ratio of 90 to 10 (Formulation No. 3).

Figure 4:
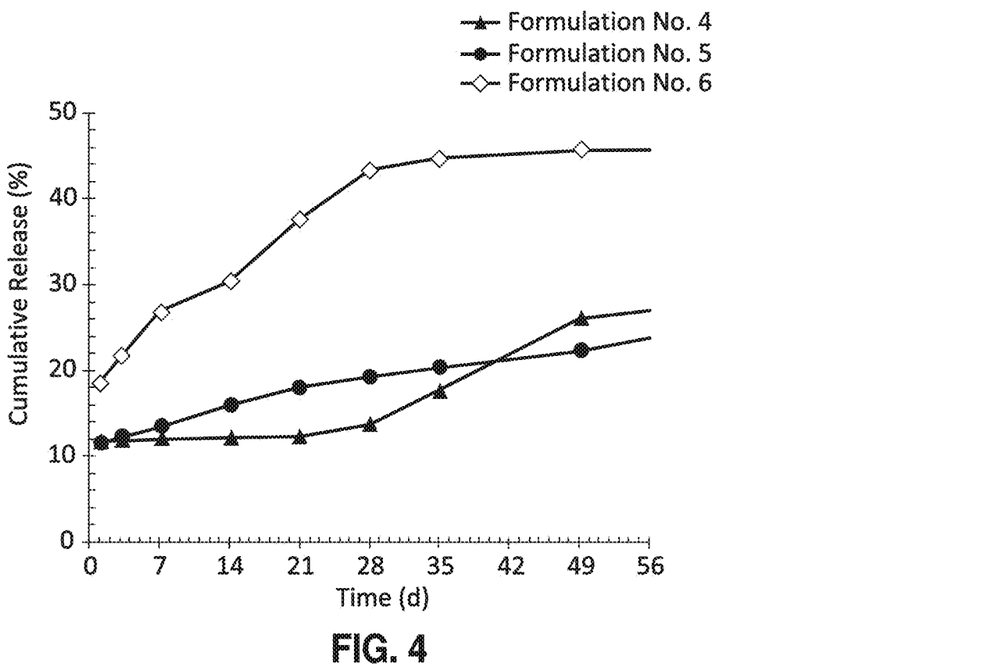
FIG. 4 shows in vitro release (SEC-HPLC) of bevacizumab from three different PLGA-bevacizumab implants (Formulation Nos. 4, 5, and 6) showing the ability to modulate the release of antibody by blending two different types of PLGA polymers (RG752S and RG502H) with RG502H facilitating release.

FIG. 4 displays the ability to modulate the release of bevacizumab from the PLGA-bevacizumab implants by altering the polymer composition, specifically by polymer blending (e.g., RG752S and RG502H). The incorporation of RG502H (50:50 lactide:glycolide with acid end group) may increase water uptake and hence facilitate release as in implants composed of a blend of RG752S and RG502H in FIG. 4. FIG. 4 compares the in vitro release of bevacizumab antibody from implants having Formulations Nos. 4, 5, and 6.

Figure 5:
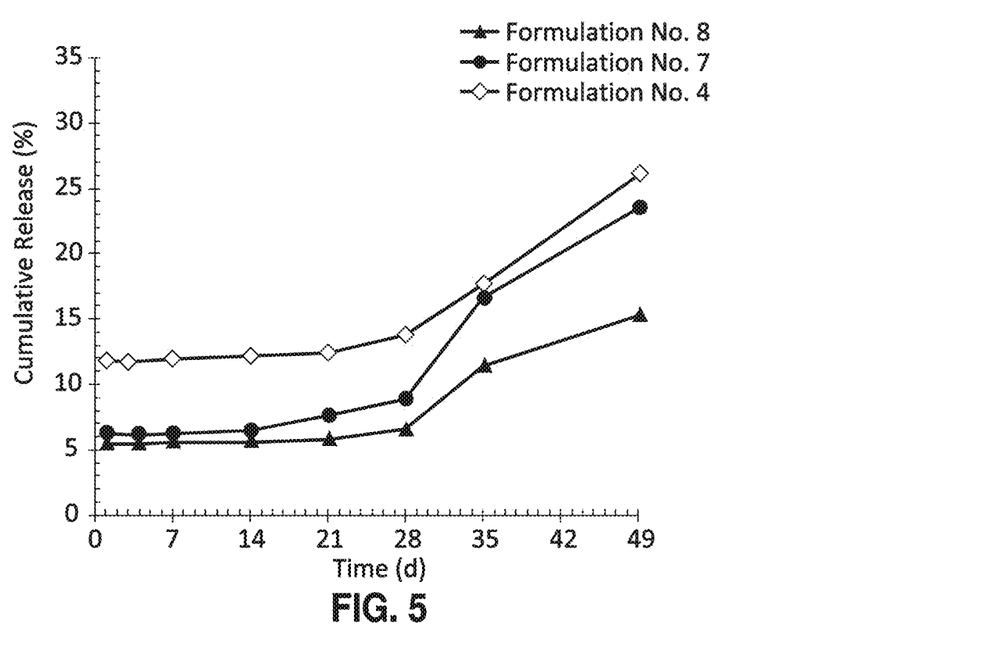
FIG. 5 shows in vitro release (SEC-HPLC) of bevacizumab from three different PLGA-bevacizumab implants (Formulation Nos. 4, 7, and 8) illustrating the ability to modify release rates of antibody from the PLGA implant by the incorporation of water soluble excipients, such as trehalose.

FIG. 5 shows the ability to modify the release of bevacizumab from the PLGA-bevacizumab implants by altering the excipient load, specifically the trehalose content. The incorporation of a water-soluble carbohydrate such as trehalose may increase water uptake and create porous channels and hence facilitate release. FIG. 5 compares the in vitro release of bevacizumab antibody from implants having Formulations Nos. 4, 7, and 8.

Figure 6:
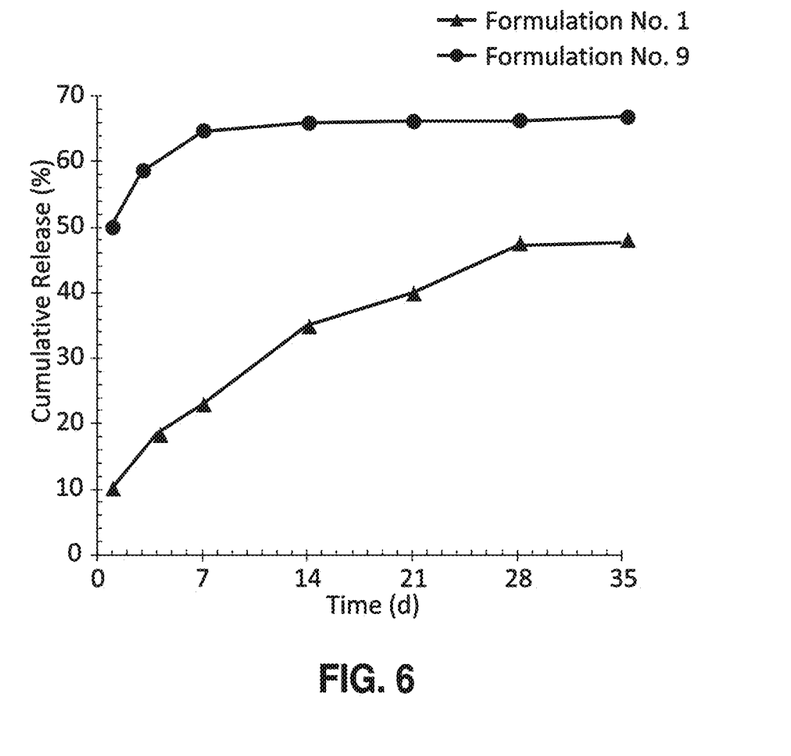
FIG. 6 shows the in vitro release profile (SEC-HPLC) of bevacizumab from two different PLGA-bevacizumab implants (Formulation Nos. 1 and 9) showing how drug load (weight percent of antibody) affects the rate of antibody release from the implant.

FIG. 6 illustrates the effect of drug load on the release profile of PLGA-bevacizumab implants. As the drug load is increased. the initial burst increases and the duration decreases. FIG. 6 compares the in vitro release of bevacizumab antibody from implants having Formulations Nos. 1 and 9.

Figure 8:
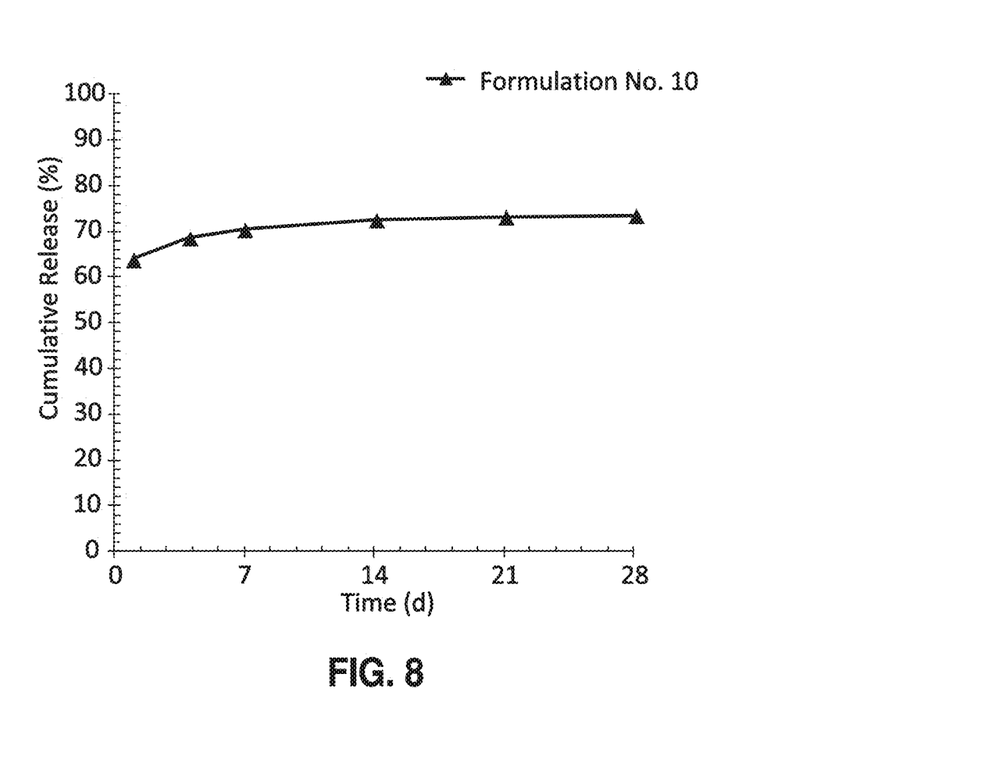
FIG. 8 shows the in vitro release profile (SEC-HPLC) of bevacizumab from a PLGA-bevacizumab implant (Formulation No. 10) showing a burst-flat release of antibody.

FIG. 8 shows a burst-flat release profile obtained from an implant having Formulation No. 10, with ~65% release of bevacizumab on day 1 and a cumulative release ~70% at day 7. Minimal to no release is observed after day 7.

Example 3

In Vivo Testing of an Antibody-Containing Implant

Figure 7:
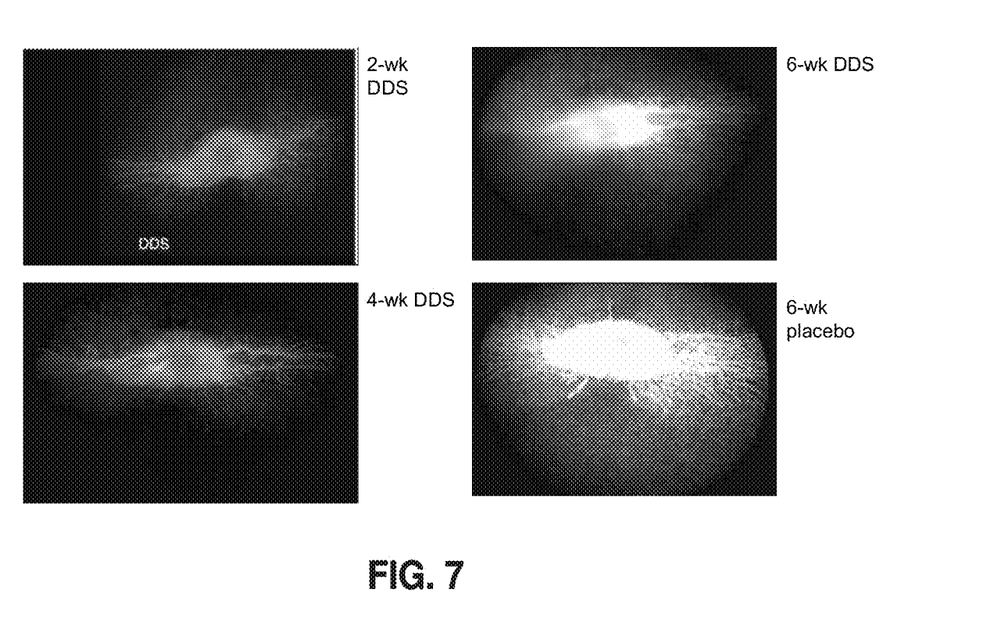
FIG. 7 shows the fluorescein images of a rabbit's vitreous in which a PLGA-bevacizumab implant (DDS: Formulation No. 1) and a PLGA placebo implant were surgically placed and VEGF challenged every two weeks illustrating knockdown of VEGF activity in the eye by the bevacizumab implant at 2 and 4 wks.

FIG. 7 shows the result from in vivo testing in which an extruded implant (Formulation No. 1) is surgically placed into the vitreous of one eye of a rabbit. In this pharmacodynamic model, the rabbit is challenged with VEGF to induce blood retinal barrier breakdown at two week intervals and images are captured by fluorescein angiography to assess how effectively the drug released from the implant is able to knock down the breakdown. The fluorescein images show that the PLGA-bevacizumab implant (DDS, drug delivery system) as compared to the PLGA implant (placebo) was effective at knocking down the breakdown at 2 and 4 weeks indicating sustained release for at least a month.

This result is significant because it demonstrates that large macromolecules, such as a full-length monoclonal antibody, can retain their tertiary structure during lyophilization, can be incorporated into a polymeric drug delivery system (DDS) that is processed at elevated temperatures, and can be released from a polymeric drug delivery in a biologically active form.

These figures and examples demonstrate the ability to formulate different bevacizumab formulations to obtain different sustained durations of release. Furthermore. these examples illustrate that large macromolecules can retain their structure and activity throughout the manufacturing process (lyophilization and extrusion at elevated temperature) and the release from the polymer. These results are significant because they demonstrate the ability to successfully deliver active monoclonal antibody from a polymeric implant for several months.

What is claimed is:

1. A method for making a biodegradable intraocular implant that provides continuous release of a protein in a biologically active form for at least 90 days after placement of the implant in an eye of a mammal, the method comprising:
   a. providing a dry powder comprising one or more proteins and, optionally, one or more excipients, salts, buffering agents, preservatives, polyelectrolytes, or combination thereof;
   b. blending the dry powder with at least two poly(D,L-lactide-co-glycolide) copolymers to form a mixture wherein one of the copolymers has an ester end group and the other copolymer has an acid end group;
   c. extruding the mixture at a temperature between 60° C. and 90° C. to form a filament;
   d. cutting the filament to form an implant 0.5 to 10 mm in length suitable for placement in an ocular region of an eye.

2. The method of claim 1, wherein the biodegradable intraocular implant effectively treats an ocular condition.

3. The method of claim 2, wherein the ocular condition is selected from the group consisting of ocular neovascularization, choroidal neovascularization, macular degeneration, and macular edema.

4. The method of claim 1, wherein the protein is an antibody, antibody fragment, DARPin, or anticalin that binds vascular endothelial growth factor (VEGF) or platelet-derived growth factor (PDGF).

* * * * *